US00PP32784P2

(12) United States Plant Patent
Bentz

(10) Patent No.: US PP32,784 P2
(45) Date of Patent: Feb. 2, 2021

(54) HEMLOCK TREE NAMED 'TRAVELER'

(50) Latin Name: ***Tsuga chinensis* x *Tsuga caroliniana***
Varietal Denomination: Traveler

(71) Applicant: The United States of America, as Represented by the Secretary of Agriculture, Washington, DC (US)

(72) Inventor: Susan E. Bentz, Beltsville, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 16/602,308

(22) Filed: Sep. 9, 2019

(51) Int. Cl.
*A01H 4/00* (2006.01)
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

(56) References Cited

PUBLICATIONS

Trademark registration to "Traveler", serial #88011596, reg # 5968310, filed Jun. 22, 2018.*
"Hemlock Woolly Adegid, Development of Resistant Hybrid Hemlocks", https://www.nrs.fs.fed.us/disturbance/invasive_species/hwa/control_management/hybrid_hemlocks/, downloaded Jun. 16, 2020, last modified May 8, 2015.*

* cited by examiner

*Primary Examiner* — Anne Marie Grunberg
(74) *Attorney, Agent, or Firm* — John D. Fado; Ariel Atkinson

(57) ABSTRACT

A new and distinct hybrid *Tsuga* cultivar tree named 'Traveler' is disclosed, characterized by a slightly weeping and graceful pyramidal habit, tolerance to hemlock woolly adelgid, and moderately slow growth rate. 'Traveler' is well-suited for use as a landscape tree in a large yard or park. It transplants well from containers.

3 Drawing Sheets

Latin name of the genus and species of the plant claimed: 'Traveler' is a hemlock that is a hybrid of *Tsuga chinensis* x *Tsuga caroliniana.*

Varietal denomination: The new hemlock claimed is of the variety denominated 'Traveler' *Tsuga chinensis* x *Tsuga caroliniana.*

BACKGROUND OF THE NEW PLANT

The present invention relates to a new and distinct variety of hemlock referred to herein as 'Traveler' that is a hybrid *Tsuga chinensis* x *Tsuga caroliniana*. This new and distinct variety is characterized in part by its high degree of resistance to hemlock woolly adelgid (HWA) and attractive growth habit for landscape. It was specifically bred for resistance to HWA, and was also selected for its symmetrical, slightly pendulous habit, and moderately slow growth rate. It may be used in residential, commercial, and possibly forest landscapes. 'Traveler' is a product of the breeding program of USDA-ARS US National Arboretum, Floral and Nursery Plant Research Unit. This new variety was selected from a group of seedlings resulting from controlled crosses made in 1992 between *T. chinensis* NA 12347 (female parent; unpatented) and a *T. caroliniana* located at the former David Fairchild Estate, Bethesda, Md. (male parent; unpatented). Resulting hybrid plants were inoculated with HWA, and 'Traveler' was among the most resistant hybrids observed. 'Traveler' also possesses an attractive pyramidal growth habit. The original tree and asexual propagules have been observed for 15 and 6 years, respectively, for both landscape merit and HWA resistance. They have shown consistent tolerance to HWA in field and container inoculation trials.

'Traveler' is intended to be used primarily as a landscape plant, although it may also prove useful in forest situations as the threat to native hemlocks (*T. canadensis*) from attack by HWA continues. The plant can be clonally propagated by cuttings taken in December or January using bottom heat or in early summer before the second flush of growth using 3000-8000 ppm indole-3-butyric Acid (IBA) or IBA combined with naphthaleneacetic acid (NAA) under mist. Rooting occurs slowly over 8-24 weeks. Propagules have been observed to be identical to the original plant in all distinguishing characteristics.

SUMMARY OF THE NEW PLANT

Plants of 'Traveler' have not been observed under all possible environmental conditions and cultural practices. The phenotype may vary somewhat with variations such as temperature and light, without, however, any variance in genotype. The following traits have been consistently observed and are unique characteristics of 'Traveler.' These characteristics in combination distinguish 'Traveler' as a new and distinct *Tsuga* cultivar:

1. Hybrid Genotype: *T. chinensis* x *T. caroliniana.*
2. Pyramidal habit with slightly pendulous branches.

3. Production of large cones (up to 3.6 cm long and 1.3 cm wide).
4. Resistance to hemlock woolly adelgid compared to *T. caroliniana* and *T. canadensis.*

BRIEF DESCRIPTION OF THE DRAWINGS

This new hemlock plant is illustrated by the accompanying figures that show certain features of the plant. The colors shown in the photographs are as true as can be reasonably obtained by conventional photographic procedures.

DETAILED BOTANICAL DESCRIPTION

Figure 1:
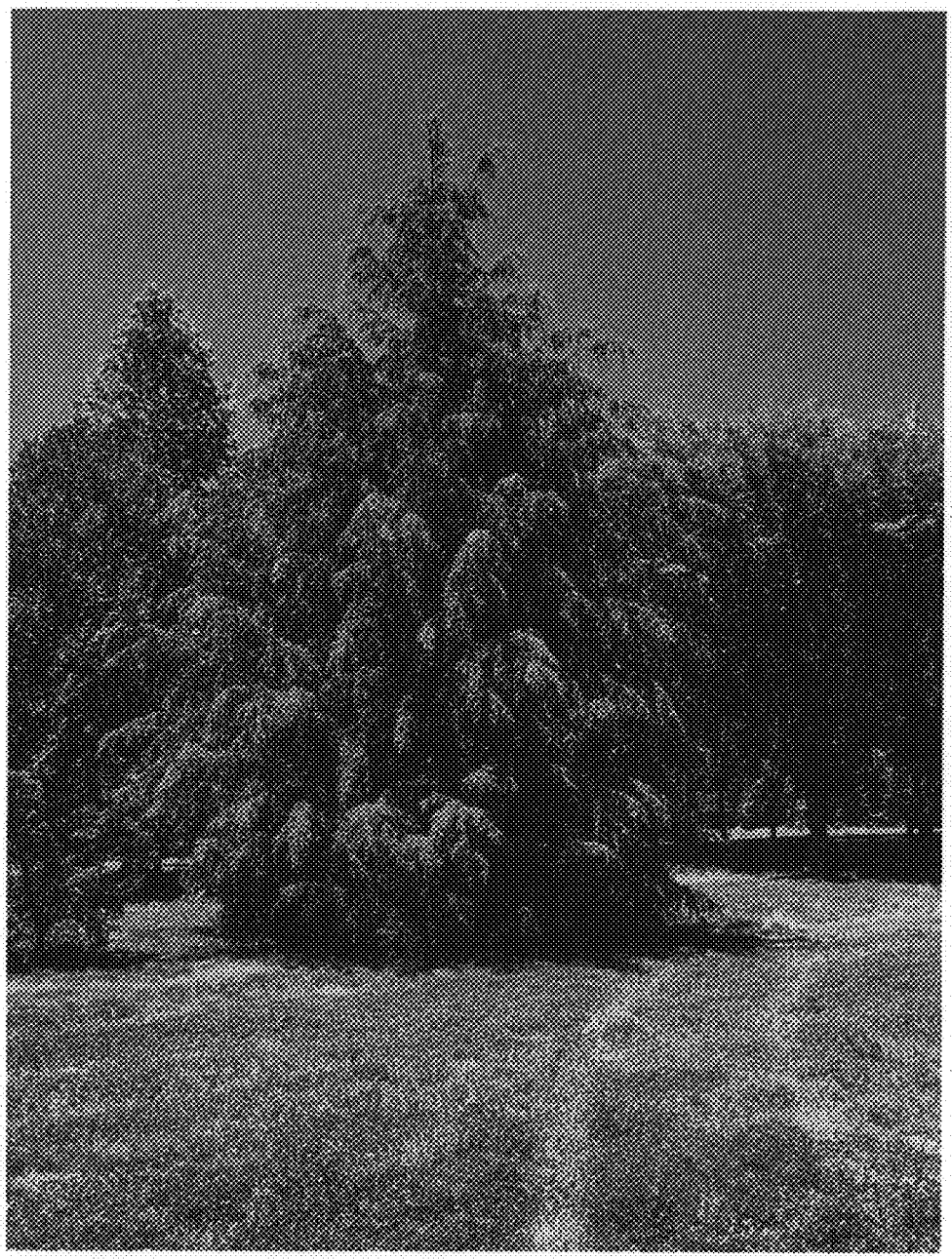
FIG. 1 illustrates in full color the mature habit of 'Traveler' grown in the field in Beltsville, Md. after 15 years. The slightly weeping branches and pyramidal habit are apparent.
Figure 2:
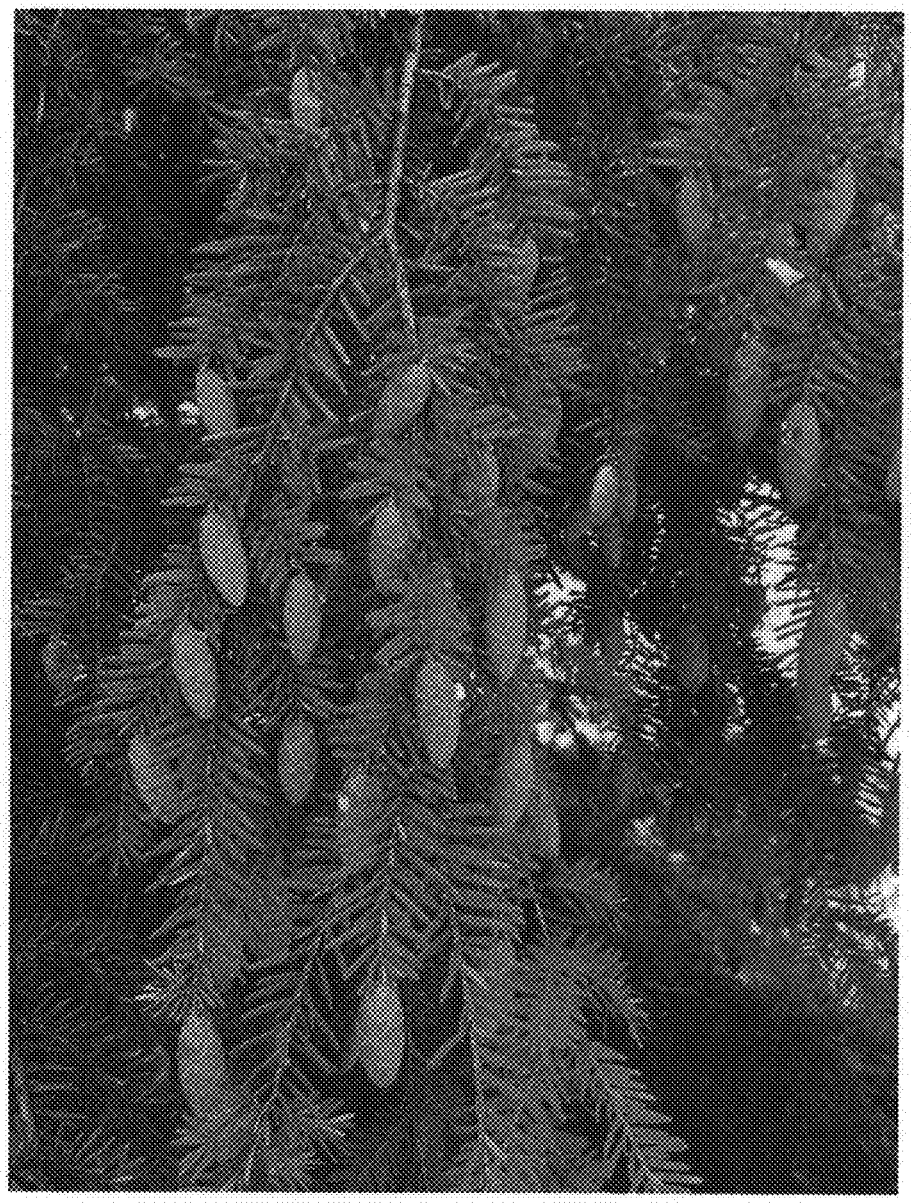
FIG. 2 shows the distinct large cones of 'Traveler' in September before they turn brown at maturity.
Figure 3:
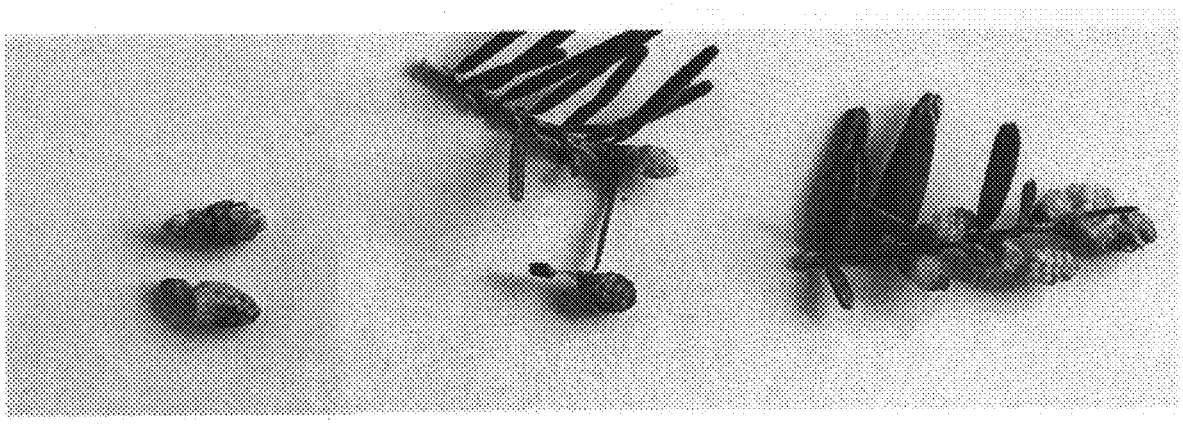
FIG. 3 shows the early female and male cones of 'Traveler' as compared to its two parents. 'Traveler' cone is on the left, followed by *T. caroliniana* and *T. chinensis.*

In the following description, color references are made to The R.H.S. Colour Chart 1966 edition, except where general terms of ordinary dictionary significance are used. Unless noted otherwise, values are taken from the mature, original plant at the age of 25 to 27 years in 2017 to 2019 growing in Beltsville, Md.

Botanical classification: *Tsuga chinensis* x *Tsuga caroliniana* 'Traveler'.

Parentage: Seedling selection of a controlled cross of *Tsuga chinensis* NA 12347 (female parent) and a *Tsuga caroliniana* located at the former David Fairchild Estate, Bethesda, Md. (male parent).

Propagation: 'Traveler' can be propagated by cuttings taken in December or January using bottom heat or early summer before the second flush of growth using 3000-8000 ppm IBA or IBA+NAA under mist. Rooting occurs slowly over 8-24 weeks. 'Traveler' was propagated asexually from terminal branch cuttings from the parent plant in Beltsville, Md. for several years and since 2006. Cuttings were taken in December or January as dormant cuttings, or in early summer between the first and second flush of new growth. Cuttings were treated with 3000-8000 ppm indole-3-butyric acid (IBA) or IBA+NAA (naphthaleneacetic acid) and stuck in a soilless mix of perlite and course sand with sphagnum or nursery mix. Trays were placed on mist benches with bottom heat at 70 degrees in winter. Rooting occurred slowly over 8-24 weeks or longer. Rooted cuttings were transplanted into individual containers in a well-drained soilless mix with additional perlite.

Rooting: Roots of cuttings form thin, dark brown roots from stubby root initials formed at the base.

Growth habit: 'Traveler' grows in a pyramidal, symmetrical pattern. The main lateral branches ascend approximately 30 degrees above horizontal. Branchlets are slightly pendulous.

Branching: The main lateral branches ascend approximately 30 degrees above horizontal. Branchlets are slightly pendulous.

Height and spread: The height is 9 meters and the width 5.5 meters in 15 years from field planting in Beltsville, Md. The total age was 25 years in 2017 and the trees were planted at 10 years of age. Trunk size of original tree is 28 cm diameter at breast height (DBH). Clonal propagules have grown to an average height of 3.5 meters in 6 years in NC.

Leaf description: Needles are not appressed and spread both laterally and upward away from the stem; spiral around the top and sides of the twigs, but not the bottom; and abaxial and adaxial surfaces smooth. Average needle length is 13.9 mm; longest needles spreading laterally 15-19 mm; shortest needles spreading upward 5-9 mm; and needles range in length from 11-17 mm in length. Needles are symmetrical, approximately 2 mm in diameter, flat and narrow with a faint groove on upper needle surface and parallel venation. The leaf apex is 1.3 mm in width and is rounded or shallowly notched with entire margins. The leaf notch is very small and is approximately 0.05 mm in depth and 0.26 mm wide when present. Needles are yellow green 145C at emergence and mature to green on the upper surface (RHS 137B). There are two white stomatal bands on the lower surface which become more prominent as needles mature. The width of each stomatal band is 0.5 mm with 6-7 rows per stomatal band measured at the midpoint of the leaf. The leaf petiole is peg-like and small, averages 1.1 mm in length and its width at the branch connection averages 0.45 mm and at its apex is 0.5 mm. There is one resin canal per needle which varies between 0.080-0.12 mm in width.

Cone description: 'Traveler' produces large quantities of cones most years. Both male and female cones are produced on the same tree in mid to late March in Maryland. Unopened female cones measured in September are yellow-green (RHS 144A) and slightly glossy. Unopened green cone length is 2.8-3.6 cm and cone width is 1.1-1.3 cm. Cones are cylindrical with blunt apices. Cones open and shed seed in October in Maryland. Mature cones are greyed-orange (RHS 164C-165D) pyramidal, short stalked and produced at tips of branches. Mature cone length is 3.1-3.7 cm and cone width is 2.7-2.8 cm. Scales of mature cones are spreading and never recurved. The cone scale bract margins are erose. The medium and outer cone scales are broadly elliptical; apex is broadly rounded; and the outer scale surface has weak parallel ridges. When old, margins are entire, thin and pale. Two seeds are produced per scale. Seeds are small, brown 0.4-0.5 cm in length and 0.13-0.18 cm in width and irregularly rectangular with tan, papery wings 1.3 cm in length and 0.5 cm in width. Germination of open-pollinated seeds is poor. Cone production has been observed in the original 'Traveler' plant, but cone production has not yet been observed on propagules to date.

Disease and pest resistance: Other than resistance to Hemlock Woolly Adelgid, no extra resistance nor susceptibility to other common pests and diseases of *Tsuga* is claimed. The original 'Traveler' hybrid has been observed for a total of 25 years in Beltsville, Md. Additionally, seven cloned individuals of the parent 'Traveler' plant were planted as part of a field trial of 20 accessions of hybrids and parent species in North Carolina where HWA would be expected to occur and have been observed for 6 years. No natural occurrence of HWA has been observed in either location. The parent hybrid tree was tested in bagged trials over two years by inoculation with crawler stage of HWA. Survival of HWA on inoculated branches was counted after 8-9 weeks. On 'Traveler', fewer HWA were observed and fewer settled adelgids survived as compared to the other hybrids and parent species in the field trial. Additionally, eight clonal propagules of this accession were observed in inoculation trials with other hybrids and parent species as young plants in a shaded polyhouse with similar results.

Flower: Flowering has been observed in the parent plant. Both male and female flowers are cone-like and produced on the same tree in mid to late March in Maryland. Female flowers emerge greyed purple (186C), turning light purple near the time of pollination. Male flowers are small, 0.5 cm in length, emerging a darker greyed purple (RHS186A), maturing to yellow and falling off after pollen shed.

COMPARISON WITH COMMERICAL CULTIVARS

There are many commercial cultivars of *T. canadensis* (over 200) from dwarf to full sized trees, with weeping, and color variations; for example, *T. canadensis* 'Albo-spica', 'Dawsoniana', and 'Sargentii'. There a small number of cultivars of *T. carolinina*, including 'Labar's Weeping' and 'Ashford'. There are no commercial cultivars of *T. chinensis* x *T. caroliniana* hybrids.

'Traveler' is intermediate in height between the two parent species. Immature male and female cones of 'Traveler' are similar in color to *T. chinensis* but are larger than cones of *T. chinensis* and similar in size to *T. caroliniana* as a species. Needle length of 'Traveler' is similar to that of both parent species, but needle arrangement is intermediate between parent species. Needles on 'Traveler' spread both laterally and upward away from stem and spiral around the top and sides of the twigs, but not the bottom. This spread contrasts with the radiating arrangement of needles around the stem in *T. caroliniana* and linear arrangement in *T. chinensis*. The timing of vegetative budbreak of 'Traveler' is similar to that of *T. chinensis*, and both are earlier than *T. caroliniana*.

While there are no commercial cultivars of *T. chinensis* or *T. chinensis* x *T. caroliniana* hybrids, plants of 'Trvaler' can be compared to the variety *T. caroliniana* 'Ashford'. Both cultivars are tree-form, but 'Traveler' is resistant to hemlock woolly adelgid, while 'Ashford' is highly susceptible to hemlock woolly adelgid. 'Traveler' may also be compared to *T. caroliniana* commercial cultivar 'La Bar's Weeping'. Plants of 'Traveler' are pyramidal with a symmetrical tree-form growth habit to 9 meters while 'La Bar's Weeping' has a weeping form that may creep across the ground if unstaked. 'La Bar's Weeping' grows to only about 1.8 meters in height and 1 meter wide if staked. 'Traveler' produces many large cones while 'La Bar's Weeping' produces many tiny cones at maturity.

The claimed plant is:

1. A new and distinct cultivar of hemlock tree, substantially as illustrated and described, characterized by a slightly weeping and graceful pyramidal habit, tolerance to hemlock woolly adelgid, and moderately slow growth rate.

* * * * *